(12) United States Patent
Metcalf et al.

(10) Patent No.: US 11,517,434 B2
(45) Date of Patent: Dec. 6, 2022

(54) ANNULOPLASTY DEVICE INCLUDING TUBE-LIKE STRUCTURE

(71) Applicant: Medtronic Vascular, Inc., Santa Rosa, CA (US)

(72) Inventors: Olivia Metcalf, Santa Rosa, CA (US); Karan Punga, San Rafael, CA (US); Matthew E. Genovese, Windsor, CA (US); Caitlin Dorff, Santa Rosa, CA (US); Emily Grimm, Petaluma, CA (US); Fatemeh Fatemi Far, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 90 days.

(21) Appl. No.: 16/710,987

(22) Filed: Dec. 11, 2019

(65) Prior Publication Data
US 2020/0188110 A1    Jun. 18, 2020

Related U.S. Application Data

(60) Provisional application No. 62/779,274, filed on Dec. 13, 2018.

(51) Int. Cl.
*A61F 2/24* (2006.01)

(52) U.S. Cl.
CPC .......... *A61F 2/2445* (2013.01); *A61F 2/2466* (2013.01); *A61F 2210/0014* (2013.01); *A61F 2220/0016* (2013.01); *A61F 2230/0091* (2013.01)

(58) Field of Classification Search
CPC .... A61F 2/2442; A61F 2/2445; A61F 2/2448; A61F 2/2454; A61F 2/2457; A61F 2/246; A61F 2/2466
See application file for complete search history.

(56) References Cited

U.S. PATENT DOCUMENTS

| | | | |
|---|---|---|---|
| 8,430,926 B2 | 4/2013 | Kirson | |
| 8,795,352 B2 | 8/2014 | O'Beirne et al. | |
| 9,517,130 B1 | 12/2016 | Alon et al. | |
| 2002/0087173 A1 | 7/2002 | Alferness et al. | |
| 2004/0236419 A1 | 11/2004 | Milo | |
| 2006/0025750 A1* | 2/2006 | Starksen | A61B 17/0682 604/510 |
| 2009/0259307 A1* | 10/2009 | Gross | A61F 2/2466 623/2.36 |

(Continued)

OTHER PUBLICATIONS

International Search Report and Written Opinion of International Application No. PCT/US2019/065887, dated Feb. 20, 2020, 15 pp.

(Continued)

*Primary Examiner* — Jennifer Dieterle
*Assistant Examiner* — Rebecca Lynee Zimmerman
(74) *Attorney, Agent, or Firm* — Medler Ferro Woodhouse & Mills PLLC

(57) ABSTRACT

In some examples, the disclosure describes an annuloplasty device that comprises a tube-like structure configured to extend around at least part of a circumference of an annulus of a cardiac or vascular valve of a patient, and at least one anchor configured to anchor the tube-like structure to the annulus. The tube-like structure is configured to decrease a distance between valve leaflets that extend from the annulus.

12 Claims, 9 Drawing Sheets

(56) References Cited

U.S. PATENT DOCUMENTS

| | | |
|---|---|---|
| 2010/0030328 A1 | 2/2010 | Sequin et al. |
| 2010/0292785 A1 | 11/2010 | Seguin et al. |
| 2011/0166649 A1 | 7/2011 | Gross et al. |
| 2012/0296417 A1 | 11/2012 | Hill et al. |
| 2012/0296419 A1 | 11/2012 | Richardson et al. |
| 2015/0127096 A1 | 5/2015 | Rowe et al. |
| 2015/0366556 A1 | 12/2015 | Khairkhahan et al. |
| 2018/0008409 A1 | 1/2018 | Kutzik et al. |
| 2018/0140421 A1* | 5/2018 | Sampson ......... A61B 17/06166 |
| 2018/0161161 A1* | 6/2018 | Yellin ................... A61F 2/2448 |

OTHER PUBLICATIONS

U.S. Appl. No. 16/710,835, filed Dec. 11, 2019, naming inventors Grimm et al.

\* cited by examiner

ANNULOPLASTY DEVICE INCLUDING TUBE-LIKE STRUCTURE

This application claims the benefit of U.S. Provisional Patent Application Ser. No. 62/779,274, filed on Dec. 13, 2018, the entire content of which is incorporated by reference herein.

TECHNICAL FIELD

This disclosure relates to heart valve repair, such as mitral valve repair.

BACKGROUND

Some patient conditions can produce valvular insufficiency or regurgitation. Valvular insufficiency or regurgitation occurs when a valve in a heart of a subject does not close completely, allowing blood to flow backwards (e.g., from the left ventricle to the left atrium), which may adversely impact the functionality of the heart.

The mitral valve includes two leaflets (anterior and posterior) attached to an annulus (e.g., a fibrous ring). In a healthy heart, the mitral valve leaflets close, or coapt, during contraction of the left ventricle and prevent blood from flowing back into the left atrium. Mitral valve regurgitation is a condition in which the leaflets of a mitral valve of a subject do not coapt properly and, as a result, blood regurgitates back into the left atrium from the left ventricle. The regurgitation of blood back into the left atrium may result in a reduced ejection volume from the left ventricle, causing the heart of the subject to work relatively hard to supply the desirable volume of blood to the body. Mitral regurgitation may occur because of different patient conditions. For example, secondary mitral regurgitation, also referred to as functional mitral regurgitation, may occur when a left ventricle dilates and causes dilation of the mitral annulus of a subject.

SUMMARY

In some aspects, this disclosure describes example annuloplasty devices, systems, and techniques for repairing a heart valve, such as, but not limited to, a mitral valve. The annuloplasty devices, systems, and techniques enable reduction in spacing between valve leaflets, may improve coaptation of the valve leaflets, and may help reduce valvular insufficiency or regurgitation.

In some examples the disclosure describes an annuloplasty device that includes a tube-like structure configured to extend around at least part of a circumference of an annulus of a cardiac or vascular valve; and at least one anchor configured to anchor the tube-like structure to the annulus, where the tube-like structure is configured to decrease a distance between valve leaflets that extend from the annulus.

In some examples the disclosure describes a system that includes a delivery device configured to access vasculature of a patient; and the annuloplasty device that includes a tube-like structure configured to extend around at least part of a circumference of an annulus of a cardiac or vascular valve; and at least one anchor configured to anchor the tube-like structure to the annulus, where the tube-like structure is configured to decrease a distance between valve leaflets that extend from the annulus, where the delivery device is configured to house the annuloplasty device in a lumen and deliver the annuloplasty device to the annulus of the cardiac or vascular valve and engage the anchors to the annulus.

In some examples the disclosure describes a method that includes advancing a delivery device through vasculature of a patient to a vascular or cardiac treatment site, where the delivery device includes a lumen housing an annuloplasty device, where the annuloplasty device includes a tube-like structure configured to extend around at least part of a circumference of an annulus of a cardiac or vascular valve; and at least one anchor configured to anchor the tube-like structure to the annulus, where the tube-like structure is configured to decrease a distance between valve leaflets that extend from the annulus; and releasing the annuloplasty device from the lumen to extend around at least part of a circumference of an annulus of a cardiac or vascular valve.

The details of one or more examples are set forth in the accompanying drawings and the description below. Other features, objects, and advantages of examples according to this disclosure will be apparent from the description and drawings, and from the claims.

DETAILED DESCRIPTION

This disclosure describes annuloplasty devices, systems, and techniques for repairing a heart valve, such as, but not limited to, a mitral valve. The annuloplasty devices, systems, and techniques enable reduction in spacing between valve leaflets, may improve coaptation of the valve leaflets, and may help reduce valvular insufficiency or regurgitation. Annuloplasty devices may include a tube-like structure and at least one anchor. The at least one anchor may be configured to engage the tube-like structure and tissue of an annulus of the heart valve or trigone of the heart valve to fix the tube-like structure to the tissue. The tube-like structure may be configured to exert a force on the tissue to urge the valve leaflets toward each other and improve coaptation of the valve leaflets.

In some examples, the at least one anchor is integral with the tube-like structure. For example, the at least one anchor may include tines or projections that are part of the tube-like structure and extend radially outward from the tube-like structure to engage tissue. In other examples, the at least one anchor is separate from the tube-like structure. For example, the at least one anchor may include a spiral anchor that spirally engages holes in the tube-like structure. As another example, the at least one anchor may include a second tube-like structure that is disposed in a bore of the first tube-like structure.

In some examples, the annuloplasty device may include a cinch device or a cinch wire. The cinch device or cinch wire may be configured to enable the tube-like structure to exert a force on the anchors to reduce spacing between the valve leaflets.

Figure 1A:
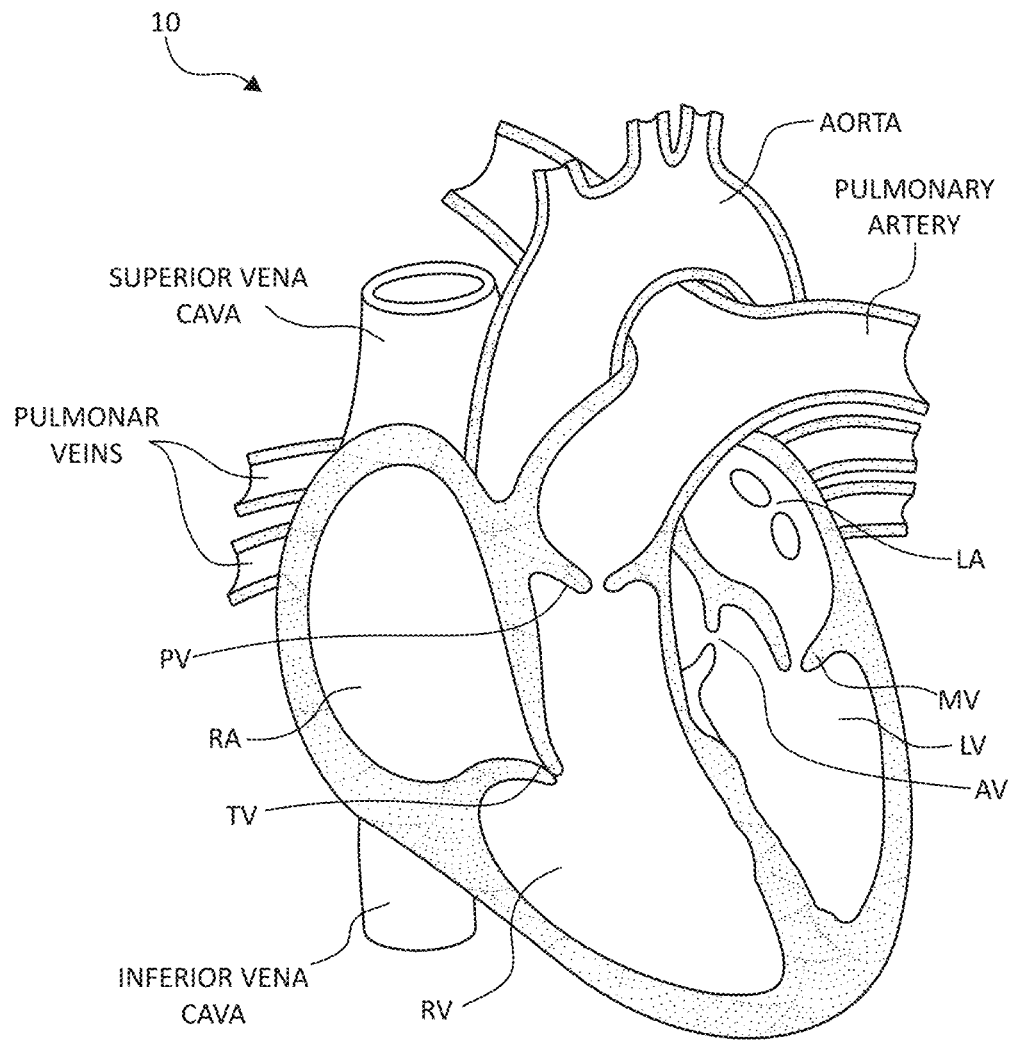
FIGS. 1A and 1B are schematic cross-sectional views of an example human heart.
Figure 1B:
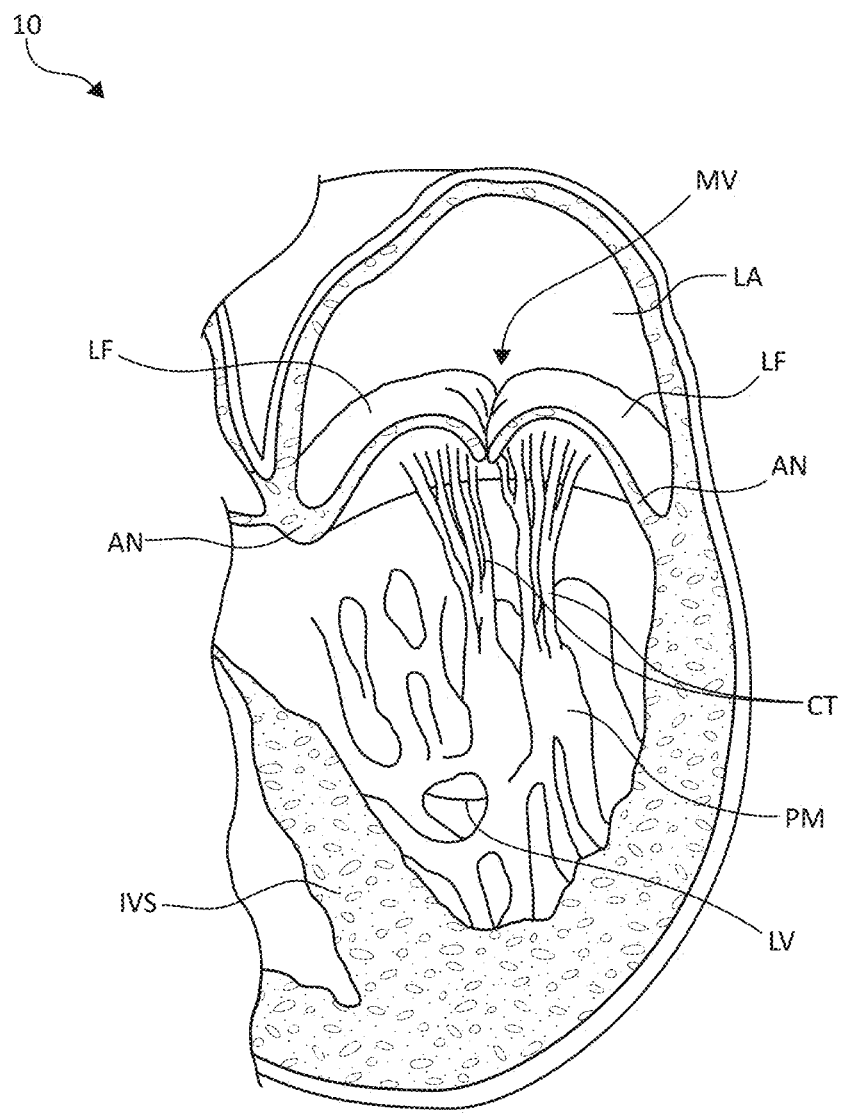

FIGS. 1A and 1B are schematic cross-sectional views of an example human heart 10. The human heart 10 is a four chambered, muscular organ that provides blood circulation through the body during a cardiac cycle. The four main chambers are the right atrium (RA) and right ventricle (RV) which supplies the pulmonary circulation, and the left atrium (LA) and left ventricle (LV) which supplies oxygenated blood received from the lungs to the remaining body. To ensure that blood flows in one direction through the heart, atrioventricular valves (tricuspid valve (TV) and mitral valve (MV)) are present between the junctions of the atrium and the ventricles, and semi-lunar valves (pulmonary valve (PV) and aortic valve (AV)) govern the exits of the ventricles leading to the lungs and the rest of the body. These valves contain leaflets (LF) or cusps that open and shut in response to blood pressure changes caused by the contraction and relaxation of the heart chambers. FIG. 1B is a schematic sectional illustration of a left ventricle LV of heart 10 showing anatomical structures and a native mitral valve MV.

The left atrium LA receives oxygenated blood from the lungs via the pulmonary veins and pumps the oxygenated blood through the mitral valve MV and into the left ventricle LV during ventricular diastole. The left ventricle LV contracts during systole and blood flows outwardly through the aortic valve AV, into the aorta and to the remainder of the body. In a healthy heart, the leaflets LF of the native mitral valve MV meet evenly at the free edges or "coapt" to close and prevent back flow of blood into the left atrium LA during contraction of the left ventricle LV. The tissue of the leaflets LF attach to the surrounding heart structure via a dense fibrous ring of connective tissue called an annulus AN. The flexible tissue of the leaflets LF of the native mitral valve MV are connected to papillary muscles PM, which extend upwardly from the lower wall of the left ventricle LV and the interventricular septum IVS, via branching tendons called chordae tendinae CT.

Mitral valve regurgitation is a condition in which the leaflets of a mitral valve of a subject do not coapt properly and, as a result, blood regurgitates back into the left atrium LA from the left ventricle LV. The regurgitation of blood back into the left atrium LA may result in a reduced ejection volume from the left ventricle LV, causing the heart of the subject to work relatively hard to supply the desirable volume of blood to the body. Mitral regurgitation may occur because of one or more patient conditions. For example, secondary mitral regurgitation, also referred to as functional mitral regurgitation, may occur when the left ventricle LV dilates and causes dilation of the mitral annulus of a subject. The leaflets LF of the valves may move apart as a result of the dilation of the left ventricle LV, which may adversely impact the ability of the leaflets to properly coapt.

In addition to or instead of being caused by dilation of the left ventricle LV, mitral valve regurgitation (or other valve regurgitation) may be caused by calcified plaque buildup in heart 10. For example, the leaflets LF of the valves (e.g., aortic valve AV or mitral valve MV) may harden and may not sufficiently coapt or meet, such that regurgitation may occur where the valve does not close completely, allowing blood to flow backwards (e.g., from the left ventricle LV to the left atrium LA). The left side of heart 10 (e.g., mitral valve MV and aortic valve AV) can be more likely to become calcified because of the higher pressures generated.

The medical devices, systems, and techniques described herein may be used to repair a valve of heart 10 via a minimally invasive medical procedure, e.g., via a transcatheter, trans-septal medical procedure that is less invasive than open heart surgery. While open heart surgeries, such as annuloplasty performed via open heart surgery, may have positive outcomes, a more minimally invasive medical procedure may also have positive outcomes while also being associated with a shorter recovery time for some patients compared to open heart surgery.

Although example devices, systems, and techniques are primarily described herein with reference to the mitral valve MV, in other examples, the example devices, systems, and techniques may be used to repair other valves in heart 10. Further, while various features are described with respect to different figures, it will be understood that features from different figures may be combined, separated, used together, or used separately across all examples shown and described.

Figure 2:
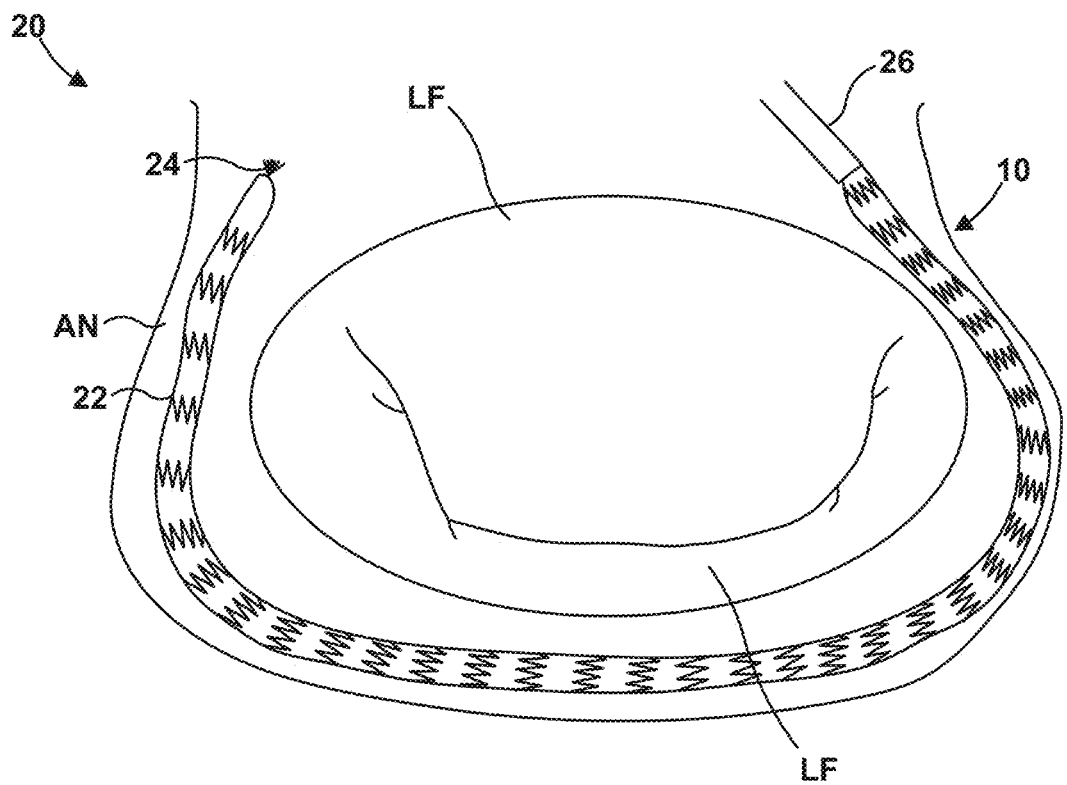
FIG. 2 is a schematic cross-sectional view of an example human heart and an example annuloplasty device including a tube-like structure.

FIG. 2 is a schematic cross-sectional view of an example human heart 10 and an example annuloplasty device 20 including a tube-like structure 22. FIG. 2 is a top cross-sectional view of human heart 10 showing the annulus AN of mitral valve MV (FIGS. 1A and 1B) and leaflets LF. Leaflets LF may include an anterior leaflet and a posterior leaflet.

Tube-like structure 22 may include a biocompatible material in a tubular shape that is configured to apply or maintain a force on annulus AN and/or leaflets LF to urge leaflets LF toward each other and improve coaptation of leaflets LF. In some examples, tube-like structure 22 may include a biocompatible metal or alloy, such as nitinol, stainless steel, a cobalt-chromium alloy, or the like. In some instances, tube-like structure 22 may include a biocompatible shape memory alloy.

Tube-like structure 22 may include a stent, a cut tube (e.g., a laser cut tube), or a tube created by joining individually formed elements. In any case, tube-like structure 22 may include a sidewall defining the shape of tube-like structure 22 and defining a bore (e.g., an inner lumen). In some examples, the bore may extend the length of tube-like structure from a proximal end of tube-like structure 22 to a distal end of tube-like structure 22. The sidewall may be shaped and sized such that another device, such as a cinch wire, a cinch device, a second tube-like structure, or the like, may extend through the bore for at least a portion of a length of tube-like structure 22.

In examples in which tube-like structure 22 includes a stent, the stent may include any suitable stent construction. For example, the stent may include a plurality of interwoven filaments that together define the sidewall of tube-like structure 22. As another example, the stent may include a spiral pattern of crowns and connection nodes configured to provide predetermined flexibility to tube-like structure 22. The spiral pattern of crowns and connection nodes may be formed by cutting a tube to remove material and leave the spiral pattern of crowns and connection nodes. As another example, the stent may include another suitable arrangement of struts.

A cut tube may include at least one cut that serves to selectively increase flexibility of the cut tube. The cuts may be oriented in a circumferential direction, a longitudinal direction, or the like. In some examples, the cuts may include spiral cut(s) that extend around a circumference of tube-like structure 22 resulting in the cut tube having a spiral or helical shape. In some examples, the cuts may additionally or alternatively include apertures or through holes configured to receive an anchor to anchor tube-like structure 22 to annulus AN and/or leaflets LF.

In some examples, tube-like structure 22 may have a pre-set shape. For example, the pre-set shape may be defined using a heat treatment. The pre-set shape is a shape toward which tube-like structure 22 recovers in the absence of an applied force. In some examples, the pre-set shape may include a radius of curvature larger than a curvature of annulus AN, such that the pre-set shape urges tube-like structure 22 radially outward toward walls of annulus AN to enable tube-like structure 22 to more closely follow the shape of annulus AN. In other examples, the pre-set shape may include a radius of curvature smaller than a curvature of annulus AN, such that the pre-set shape urges tube-like structure 22 radially inward toward coaptation surfaces of leaflets LF. When tube-like structure 22 is anchored to annulus AN and/or leaflets LF, the pre-set shape that urges tube-like structure 22 radially inward toward may exert a force on annulus AN and/or leaflets LF to increase coaptation of leaflets LF.

Tube-like structure 22 is configured to extend along a predetermined length of annulus AN. In some examples, tube-like structure 22 may extend from a first trigone attached to annulus AN to a second trigone attached to annulus AN. In other examples, tube-like structure 22 may extend from adjacent to a first leaflet LF to a second leaflet LF. In still other examples, tube-like structure 22 may extend substantially around a perimeter of annulus AN.

Annuloplasty device 20 also includes at least one anchor 24. At least one anchor 24 may include any structure configured to engage tube-like structure 22 to annulus AN and/or leaflets LF and retain tube-like structure 22 substantially in place relative to annulus AN and/or leaflets LF. In some examples, at least one anchor 24 includes a plurality of anchors, and respective anchors of the plurality of anchors may be positioned along a length of tube-like structure 22. In other examples, at least one anchor 24 may include a single anchor that extends along at least part of a length of tube-like structure 22.

In some examples, at least one anchor 24 includes a helix or double helix that is configured to be advanced into tissue of heart 10, e.g., annulus AN and/or leaflets LF. The helix or double helix may optionally include an attachment, such as a hook, loop, or the like that is configured to engage tube-like structure 22 or another portion of annuloplasty device 20 to substantially retain tube-like structure 22 relative to the anchor 24. In this way, the at least one anchor 24 may be configured to substantially retain tube-like structure 22 relative to a location of tissue of heart 10, such as a location of annulus AN and/or leaflets LF. At least one anchor 24 thus allows application of force form tube-like structure 22 to tissue of heart 10 at selected locations of heart 10.

FIG. 2 also illustrates a delivery device 26 for annuloplasty device 20. In the example of FIG. 2, delivery device 26 includes a catheter. The catheter may define an internal lumen that extends from proximate a proximal end of the catheter to proximate a distal end of the catheter (e.g., may extend from the proximal end to the distal end). The lumen may be configured to house annuloplasty device 20 during percutaneous introduction of the catheter into vasculature of a patient and advancing of the distal end of the catheter to the treatment location, such as the left atrium LA. In some examples, the catheter may be used with a guidewire, a guide catheter, or the like, to facilitate introduction of the catheter into vasculature of a patient and advancing of the distal end of the catheter to the treatment location. In some examples, the catheter includes a steerable shaft and/or distal tip to allow a clinician to control positioning of the distal tip relative to anatomical structures, such as heart 10. In some implementations, the catheter may access left atrium LA trans-septally.

The catheter is also configured to deploy annuloplasty device 20, e.g., tube-like structure 22 and at least one anchor 24 in position proximate annulus AN and engage the at least one anchor 24 with tissue of heart 10, e.g., with annulus AN and/or leaflets LF. In some examples, to facilitate positioning of the catheter, annuloplasty device 20, or both, within the treatment location, a distal portion of the catheter may include at least one radiographic marker configured to be visualized using a radiographic technique.

Annuloplasty device 20, including tube-like structure 22 and at least one anchor 24 may be formed in any one or more of a variety of configurations. FIGS. 3-10 are conceptual diagrams illustrating various aspects of examples of tube-like structure 22 and at least one anchor 24. Although features of annuloplasty device 20 are described with reference to different examples, it will be appreciated that features of the annuloplasty devices described herein, including those illustrated in FIGS. 3-10, may be used in any combination.

Figure 3:
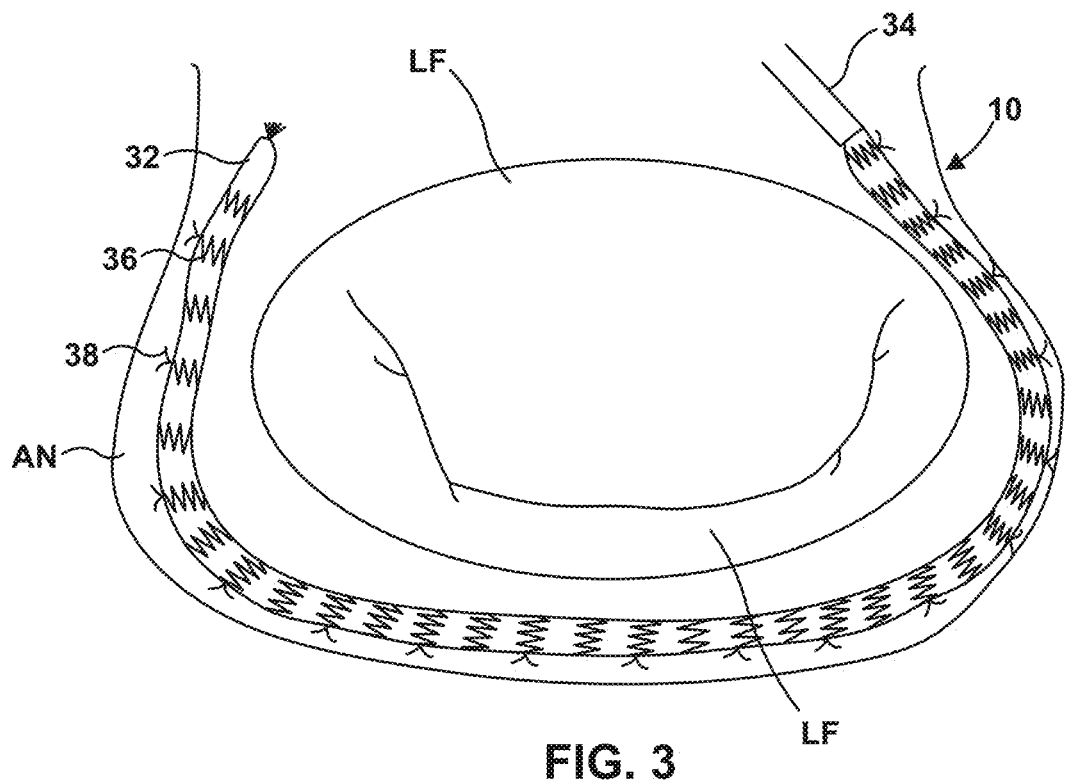
FIG. 3 is a schematic cross-sectional view of an example human heart and an example annuloplasty device including a first tube-like structure and a second tube-like structure including a plurality of anchors.

FIG. 3 is a schematic cross-sectional view of an example human heart 10 and an annuloplasty device 30 including a first tube-like structure 32 and a second tube-like structure 36 including a plurality of anchors 38. Second tube-like structure 36 may be arranged coaxially within first tube-like structure 32, or vice versa. FIG. 3 also illustrates a catheter 34 configured to introduce annuloplasty device 30 to heart 10. Catheter 34 may be similar to or substantially the same as any other catheter described herein, including catheter 26 of FIG. 2.

First tube-like structure 32 may be similar to or substantially the same as any other tube-like structures described herein, including tube-like structure 22 of FIG. 2. In some examples, first tube-like structure 32 may include a pre-set shape configured to urge a sidewall of first tube-like structure 32 into contact with tissue of annulus AN and/or leaflets LF, e.g., a pre-set structure configured to cause first tube-like structure 32 to return toward a radius of curvature larger than a curvature of annulus AN.

Second tube-like structure 36 may include a biocompatible material in a tubular shape. In some examples, second tube-like structure 36 may include a biocompatible metal or alloy, such as nitinol, stainless steel, a cobalt-chromium alloy, or the like. In some instances, second tube-like structure 36 may include a biocompatible shape memory alloy.

Second tube-like structure 36 may include a stent or a laser-but tube. In either case, second tube-like structure 36 may include a sidewall defining the shape of second tube-like structure 36 and defining a bore. In some examples, the bore may extend the length of second tube-like structure 36 from a proximal end of second tube-like structure 36 to a distal end of second tube-like structure 36. The sidewall may be shaped and sized such that another device, such as a cinch wire, a cinch device, a second tube-like structure, or the like, may extend through the bore for at least a portion of a length of second tube-like structure 36.

Additionally, the sidewall of second tube-like structure 36 may be shaped and sized such that second tube-like structure 36 may be disposed in the bore of first tube-like structure 32. For example, the sidewall of second tube-like structure 36 may have an outer diameter or outer circumference that is less than an inner diameter or an inner circumference of the sidewall of first tube-like structure 32. In some examples, the side wall of second tube-like structure 36 may have an outer diameter or outer circumference that is sufficiently close to the inner diameter or the inner circumference of the sidewall (e.g., the inner circumference of the bore) of first tube-like structure 32. First and second tube-like structures 32, 36 are configured such that when second tube-like structure 36 is within a bore of first tube-like structure 32, plurality of anchors 38 extend radially outward through openings in the sidewall of first tube-like structure 32 to engage tissue of heart 10 (e.g., annulus AN and/or leaflets LF).

In examples in which second tube-like structure 36 includes a stent, the stent may include any suitable stent construction. For example, the stent may include a plurality of interwoven filaments that together define the sidewall of second tube-like structure 36. As another example, the stent may include a spiral pattern of crowns and connection nodes configured to provide predetermined flexibility to second tube-like structure 36. The spiral pattern of crowns and connection nodes may be formed by cutting a tube to remove material and leave the spiral pattern of crowns and connection nodes. As another example, the stent may include another suitable arrangement of struts.

A laser cut tube may include at least one cut that serves to selectively increase flexibility of the laser cut tube. The cuts may be oriented in a circumferential direction, a longitudinal direction, or the like. In some examples, the cuts may include spiral cut(s) that extend around a circumference of second tube-like structure 36 resulting in the laser cut tube having a spiral or helical shape.

In some examples, second tube-like structure 36 may have a pre-set shape. For example, the pre-set shape may be defined using a heat treatment. The pre-set shape is a shape toward which second tube-like structure 36 recovers in the absence of an applied force. In some examples, the pre-set shape may include a radius of curvature larger than a curvature of annulus AN, such that the pre-set shape urges second tube-like structure 36 radially outward toward walls of annulus AN to enable second tube-like structure 36 to more closely follow the shape of annulus AN. Such a pre-set shape also may urge the sidewall of first tube-like structure 32 into contact with tissue of heart 10 (e.g., annulus AN and/or leaflets LF) and may urge the plurality of anchors 38 into engagement with tissue of heart 10 (e.g., annulus AN and/or leaflets LF).

Plurality of anchors 38 may be formed integrally with second tube-like structure 32 or otherwise attached to second tube-like structure 32. As used herein, formed integrally means that the structures are part of a single, inseparable structure. For example, plurality of anchors 38 may be defined by laser cutting as part of the process of laser cutting second tube-like structure 32. In other examples, plurality of anchors 38 may be welded to second tube-like structure 32, mechanically coupled to second tube-like structure 32, or the like. Plurality of anchors 38 may have any suitable shape, including, for example, substantially straight or curved tines, hooks, helices, double helices, or the like.

Plurality of anchors 38 are distributed along a length of second tube-like structure 32. The distribution of anchors 38 affects the points at which force can be applied to tissue of heart 10 via first tube-like structure 32 and anchors 38. In some examples, plurality of anchors 38 may be distributed substantially evenly along the length of second tube-like structure 36. In other examples, plurality of anchors 44 may be distributed unevenly along the length of tube-like structure 42. Further, second tube-like structure 36 may extend along at least part of a length of first tube-like structure 32. In some examples, second tube-like structure 36 may extend substantially along an entire length of first tube-like structure 32.

In some examples, first tube-like structure 32 may have a pre-set shape that urges plurality of anchors 38 into engagement with tissue of heart 10, e.g., annulus AN. For example, first tube-like structure 32 may have a pre-set shape with a radius of curvature larger than curvature of annulus AN.

Figure 4:
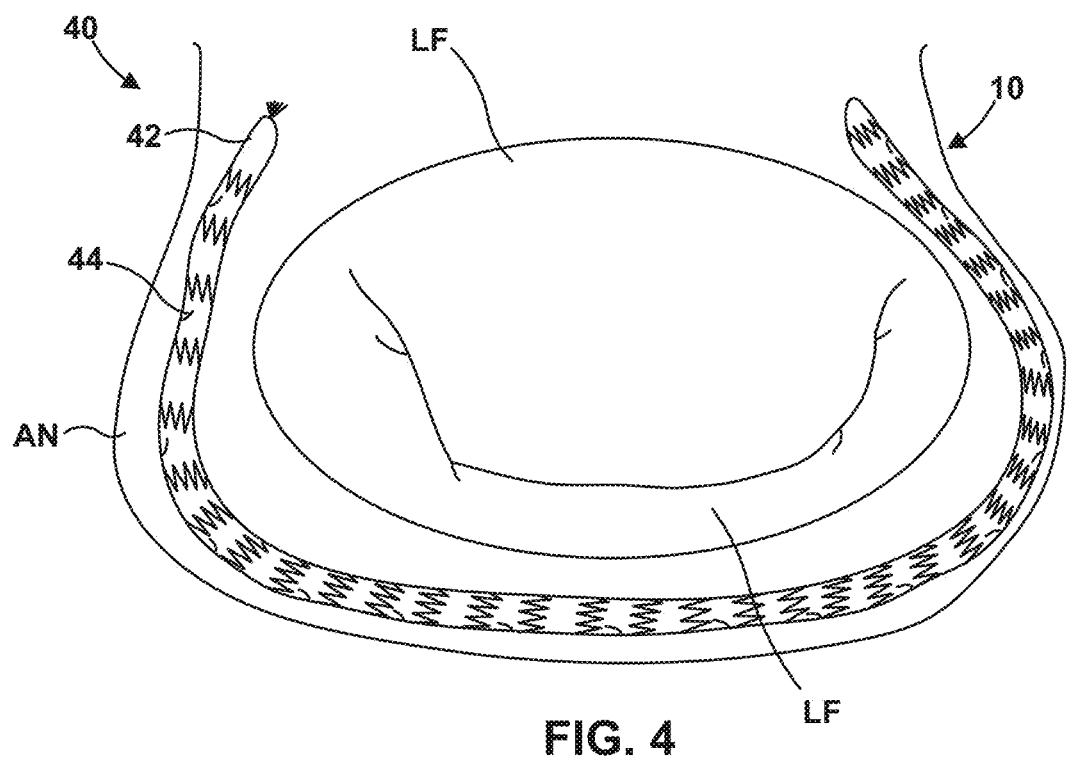
FIG. 4 is a schematic cross-sectional view of an example human heart and an example annuloplasty device including a tube-like structure that includes a plurality of anchors, with the plurality of anchors in an undeployed configuration.

FIG. 4 is a schematic cross-sectional view of an example human heart 10 and an annuloplasty device 40 including a tube-like structure 42 that includes a plurality of anchors 44. Tube-like structure 42 may be similar to or substantially the same as any other tube-like structures described herein, including tube-like structure 22, aside from the differences described herein.

Plurality of anchors 44 may be attached to or formed integrally with tube-like structure 42. For example, plurality of anchors 44 may be defined by laser cutting as part of the process of laser cutting tube-like structure 42. In other examples, plurality of anchors 44 may be welded to tube-like structure 42, mechanically coupled to tube-like structure 42, or the like. Plurality of anchors 44 may have any suitable shape, including, for example, substantially straight or curved tines, hooks, helices, double helices, or the like.

Plurality of anchors 44 may be distributed along a length of tube-like structure 42. The distribution of anchors 44 affects the points at which force can be applied to tissue of heart 10 via tube-like structure 42 and anchors 44. In some examples, plurality of anchors 44 may be distributed substantially evenly along the length of tube-like structure 42. In other examples, plurality of anchors 44 may be distributed unevenly along the length of tube-like structure 42. For example, plurality of anchors 44 may be distributed proximate to a distal end of tube-like structure 42 and proximate to a proximal end of tube-like structure 42 and absent from a medial portion of tube-like structure 42.

Plurality of anchors 44 may be movable between an undeployed configuration and a deployed configuration. In the undeployed configuration shown in FIG. 4, free ends of plurality of anchors 44 may be oriented toward the bore of tube-like structure 42 such that plurality of anchors 44 do not engage tissue adjacent to the sidewall of tube-like structure 42.

Figure 5:
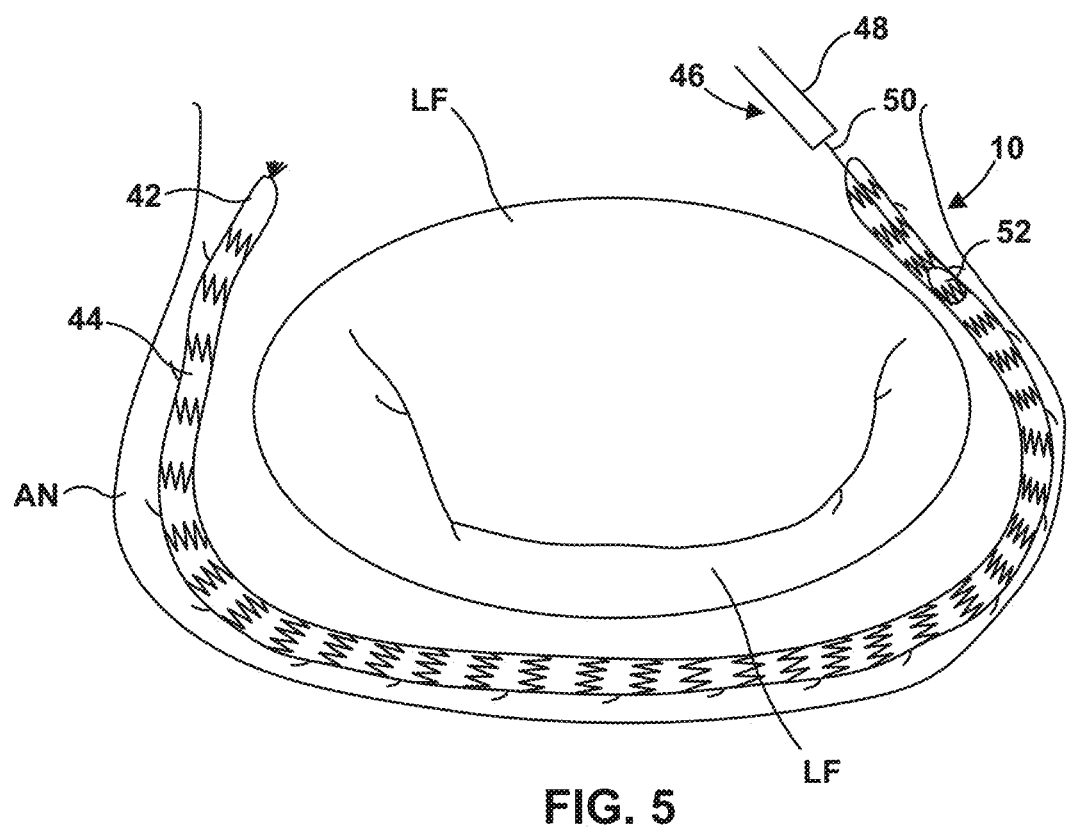
FIG. 5 is a schematic cross-sectional view of an example human heart and an example annuloplasty device including a tube-like structure that includes a plurality of anchors, with the plurality of anchors in a deployed configuration.

FIG. 5 is a schematic cross-sectional view of an example human heart 10 and annuloplasty device 40, with the plurality of anchors 44 in a deployed configuration. In the deployed configuration, free ends of plurality of anchors 44 are oriented away from the bore of tube-like structure 42 (i.e., outwards from sidewall of tube-like structure 42). Plurality of anchors 44 are configured to engage tissue of heart 10 (e.g., annulus AN and/or leaflets LF) in the deployed configuration.

As shown in FIG. 5, in some examples, plurality of anchors 44 may be moved from the undeployed configuration to the deployed configuration using a delivery device 46. Delivery device 46 includes an elongate member 48 that defines at least one lumen and an expandable balloon catheter 50. Like delivery device 26, the at least one lumen may be configured to house and release annuloplasty device 40 to the treatment site (e.g., adjacent annulus AN). Further, the at least one lumen may be configured to house and release balloon catheter 50. Balloon catheter 50 includes an expandable balloon 52 configured to expand and contract from an expanded configuration to a contracted configuration and vice versa under control of a clinician manipulating balloon catheter 50. For example, expandable balloon 52 may be configured to expand in response to application of pressure to an interior of expandable balloon 52, e.g., using a fluid, and contract in response to removal of the application of pressure to the interior of expandable balloon 52.

To move plurality of anchors 44 from the undeployed configuration to the deployed configuration, balloon catheter 50 may be advanced from delivery device 46 to position expandable balloon 52 within the bore of tube-like structure 42 adjacent to one or more anchor of the plurality of anchors 44. Expandable balloon 52 then may be expanded to exert force again the one or more anchor and move the one or more anchor from the undeployed configuration to the deployed configuration. The anchor may be configured to remain in the deployed configuration, even after contraction of expandable balloon 52. Expandable balloon 52 then may be contracted, balloon catheter 50 manipulated to move expandable balloon 52 adjacent to another one or more anchor of the plurality of anchors, and expandable balloon 52 expanded to exert force again the one or more anchor and move the one or more anchor from the undeployed configuration to the deployed configuration. This technique may be repeated until all anchors of the plurality of anchors 44 are in the deployed configuration.

In some examples, selectively deploying anchors 44 may facilitate the implantation of annuloplasty device 40 because a clinician may first confirm annuloplasty device 40 is at a suitable location within heart 10 before deploying the anchors 44 and fixing annuloplasty device 40 in place within heart 10.

In some examples, rather than including a single tube-like structure 42, the example shown in FIGS. 4 and 5 may include multiple, distinct tube-like structures deployed using respective catheters.

Figure 6:
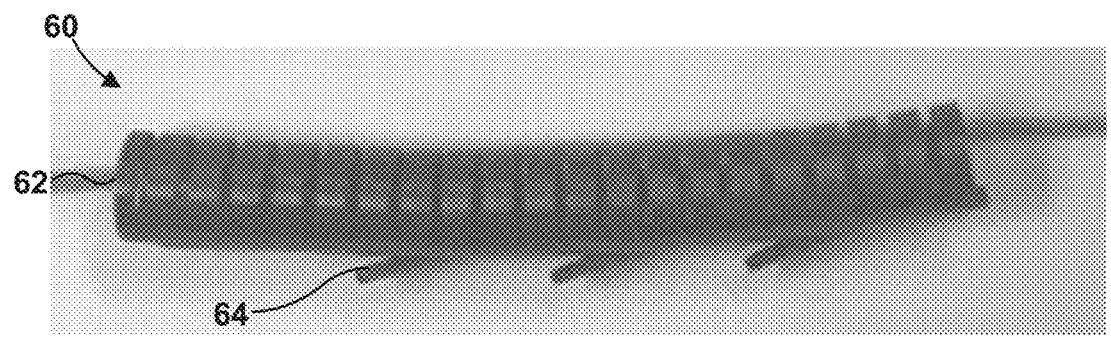
FIG. 6 is an image of an example annuloplasty device including a tube-like structure and a plurality of anchors that are biased to engage with tissue.

In some examples, a tube-like member may include anchors that are biased to engage with tissue. For example, FIG. 6 is an image of an example an annuloplasty device 60 including a tube-like structure 62 and a plurality of anchors 64 that are biased to engage with tissue. Tube-like structure 62 may be similar to or substantially the same as any other tube-like structures described herein, including tube-like structure 22 of FIG. 2, aside from the differences described herein. In the example of FIG. 6, tube-like structure 62 includes a cut tube.

Tube-like structure 62 also includes plurality of anchors 64. In some examples, plurality of anchors 64 are integral to tube-like structure 62. In other examples, plurality of anchors 64 are attached to tube-like structure 62. Plurality of anchors 64 are all oriented with free ends oriented outward away from the bore of tube-like structure 62 in a single direction, such that, by moving tube-like structure 62 in the direction of the free ends of the plurality of anchors 64, the plurality of anchors 64 may be made to engage tissue of a heart (e.g., tissue of an annulus AN or leaflets LF (FIGS. 1A and 1B)).

In other examples, at least some of anchors 64 are configured to self-expand. When annuloplasty device 60 is positioned within an inner lumen of an elongate member (e.g., elongate member 48 shown in FIG. 5), the anchors 64 may be held in an undeployed configuration by elongate member 48. As each self-expandable anchor 64 is deployed from the elongate member of the delivery device, the respective self-expandable anchor 64 may expand radially outwards into the deployed configuration.

Figure 7:
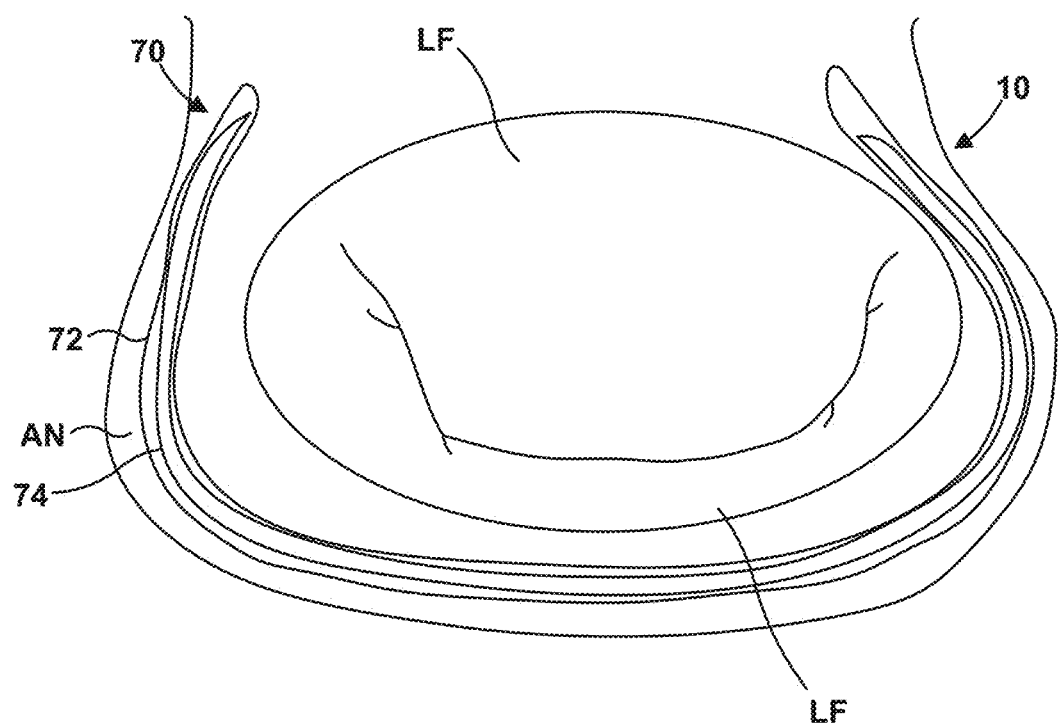
FIG. 7 is a line diagram of an example annuloplasty device including a tube-like structure and a cinching device in a bore of the tube-like structure.

A radially inward force may be exerted by or on the tube-like structure of any one of FIGS. 3-6 using one or more of a variety of mechanisms. For example, as described above, in some implementations the tube-like structure may have a pre-set structure with a radius of curvature less than the radius of curvature of annulus AN, such that when the tube-like structure is engaged to the annulus using at least one anchor, the restorative force caused by the tube-like structure recovering toward its pre-set shape exerts a radially inward force on the annulus AN. FIG. 7 is a line diagram of an example annuloplasty device 70 including a tube-like structure 72 and a cinching device 74 in a bore of tube-like structure 72, illustrating another example mechanism for exerting a radially inward force on tube-like structure 72. Tube-like structure 72 may be similar to or substantially the same as any other tube-like structures described herein, including tube-like structure 22 of FIG. 2, aside from the differences described herein.

Cinching device 74 may include a wire, tube-like device, or the like, configured to fit within the bore of tube-like structure 72 and exert a radially inward force on tube-like structure 72 (e.g., an interior surface of the sidewall of tube-like structure 72). Cinching device 74 may have a pre-set shape with a radius of curvature less than the radius of curvature of tube-like structure 72. In this way, cinching device 74 may exert a restorative force on tube-like structure 72 as cinching device 74 recovers toward its pre-set shape. In some examples, cinching device 74 may include a shape memory alloy, such as a Ni—Ti alloy. Cinching device 74 may extend in the bore along at least a portion of the length of tube-like structure 72, such as along an entire length of tube-like structure 72.

Figure 8:
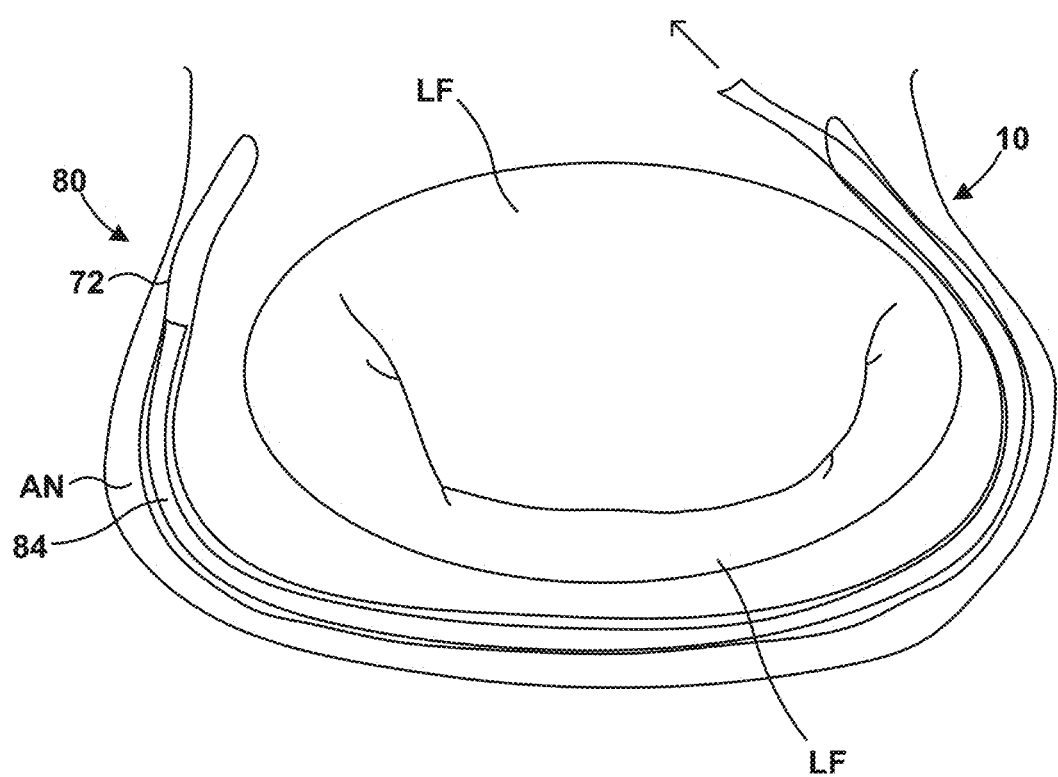
FIG. 8 is a schematic view of an example annuloplasty device including a tube-like structure and a stylet in a bore of the tube-like structure.
Figure 9:
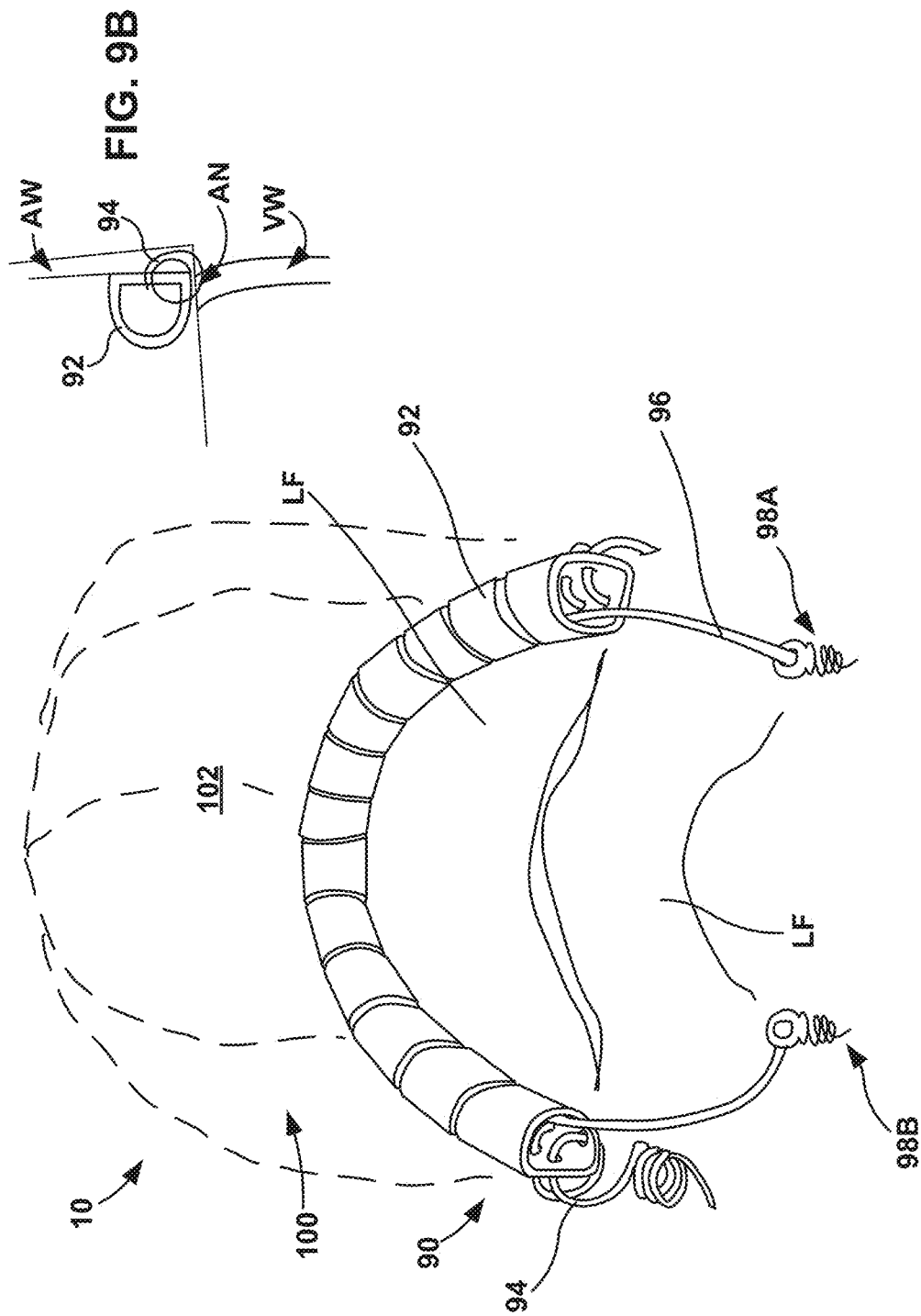
FIG. 9A is a schematic partial cross-sectional view of an example human heart and an annuloplasty device including a tube-like structure, a spiral anchor, and a cinch wire.
FIG. 9B is a cross-sectional view of the human heart of FIG. 9A illustrating a portion of atrial wall, annulus, and ventricular wall.

FIG. 8 is a schematic view of an example annuloplasty device 80 including a tube-like structure 82 and a removable stylet 84 in a bore of tube-like structure 82. Tube-like structure 82 may be similar to or substantially the same as any other tube-like structures described herein, including tube-like structure 22 of FIG. 2, aside from the differences described herein. Removable stylet 84 may be disposed in the bore of tube-like structure 82 during introduction to the treatment site and engagement of tube-like structure 82 with tissue using at least one anchor. Removable styles 84 may include a biocompatible material, such as a biocompatible shape memory alloy. Removable stylet 84 may have a pre-set shape with a radius of curvature larger than a radius of curvature of tube-like structure 82. For example, removable stylet 84 may have a pre-set shape with a radius of curvature that approximates or is substantially the same as the annulus or other physiological structure to which tube-like structure 82 is to be engaged. In this way, removable stylet 84 may facilitate positioning and engagement of tube-like structure 82 with the annulus or other physiological structure.

Once tube-like structure 82 has been positioned and engaged with tissue, removable stylet 84 may be removed from the bore of tube-like structure 82. Since tube-like structure 82 has a radius of curvature than removable stylet 84, removal of removable stylet 84 from the bore of tube-like structure 82 allows tube-like structure 82 to restore toward its pre-set shape with a smaller radius of curvature. This exerts a restorative, radially inward force on the at least one anchor, and, thus, the tissue to which tube-like structure 82 is engaged.

FIG. 9A is a schematic partial cross-sectional view of an example human heart 10 and an example annuloplasty device 90 including a tube-like structure 92, a spiral anchor 94, and a cinch wire 96. FIG. 9A illustrates posterior wall 102 of the left atrium 100 and anterior and poster leaflets LF. FIG. 9B is a cross-sectional view of human heart 10 illustrating a portion of atrial wall AW, annulus AN, and ventricular wall VW. Tube-like structure 92 may be similar to or substantially the same as any other tube-like structures described herein, including tube-like structure 22 of FIG. 2, aside from the differences described herein.

In some examples, tube-like structure 92 may have a pre-set shape that includes a radius of curvature that is larger than a radius of curvature of annulus AN. In other examples, tube-like structure 92 may have a pre-set shape that includes a radius of curvature that is substantially the same as or smaller than a radius of curvature of annulus AN. Tube-like structure 92 defines a bore through which cinch wire 96 extends. Further, tube-like defines a plurality of apertures or through holes through which spiral anchor 94 extends. Spiral anchor 94 may include any suitable material, such as any material described herein for a tube-like structure or anchor. For example, spiral anchor 94 may include a biocompatible metal or alloy, such as a biocompatible shape memory alloy, a Ni—Ti alloy, stainless steel, a Co—Cr alloy, or the like.

Cinch wire 96 extends through the bore of tube-like structure 92 from a first end of tube-like structure 92 to a second end of tube-like structure 92. A first end of cinch wire 96 is attached to a first helical anchor 98A and a second end of cinch wire 96 is attached to a second helical anchor 98B (collectively, "helical anchors 98"). Helical anchors 98 engage tissue of heart 10, such as annulus AN. For example, first helical anchor 98A may engage tissue of a first trigone and second helical anchor 98B may engage tissue of a second trigone. In some examples, the first end of cinch wire 96 may be pre-attached to first helical anchor 98A and the second end of cinch wire 96 may be attached to second helical anchor 98B after spiral anchor 94 is deployed and cinch wire 96 is tightened. Cinch wire 96 may include any suitable material, such as any material described herein for a tube-like structure or anchor. For example, cinch wire 96 may include a biocompatible metal or alloy, such as a biocompatible shape memory alloy, a Ni—Ti alloy, stainless steel, a Co—Cr alloy, or the like.

To deploy annuloplasty device 90, a delivery device may deploy first helical anchor 98A (with cinch wire 96 pre-attached) and engage first helical anchor 98A with tissue, such as a first trigone and/or annulus AN. The delivery device then may deploy tube-like structure 92 while approximately circumnavigating annulus AN to help tube-like structure 92 seat on annulus AN. During deployment of tube-like structure 92, cinch wire 96 already extends through the bore of tube-like structure 92.

Once tube-like structure 92 is deployed and seated on annulus AN, the delivery device may engage spiral anchor 94 with tube-like structure 92. For example, the delivery device be manipulated to torque spiral anchor 94 to cause spiral anchor 94 to spirally advance through the apertures or through holes defined in tube-like structure 92 while engaging tissue of annulus AN and/or atrial wall AW. The delivery device may continue to be manipulated to torque spiral anchor 94 until spiral anchor 94 has engaged tube-like structure 92 along a predetermined length of tube-like structure 92, e.g., an entire length of tube-like structure 92.

After spiral anchor 94 has engaged tube-like structure 92 along the predetermined length of tube-like structure 92, the free end of cinch wire 96 (e.g., the end not connected to first helical anchor 98A) may be pulled by the delivery device to tighten tube-like structure and pull the anchored section of the annulus toward the helical anchors 98. The delivery device may then crimp the cinch wire to second helical anchor 98B to hold cinch wire 96 and tube-like structure 92 in the cinched position.

Figure 10:
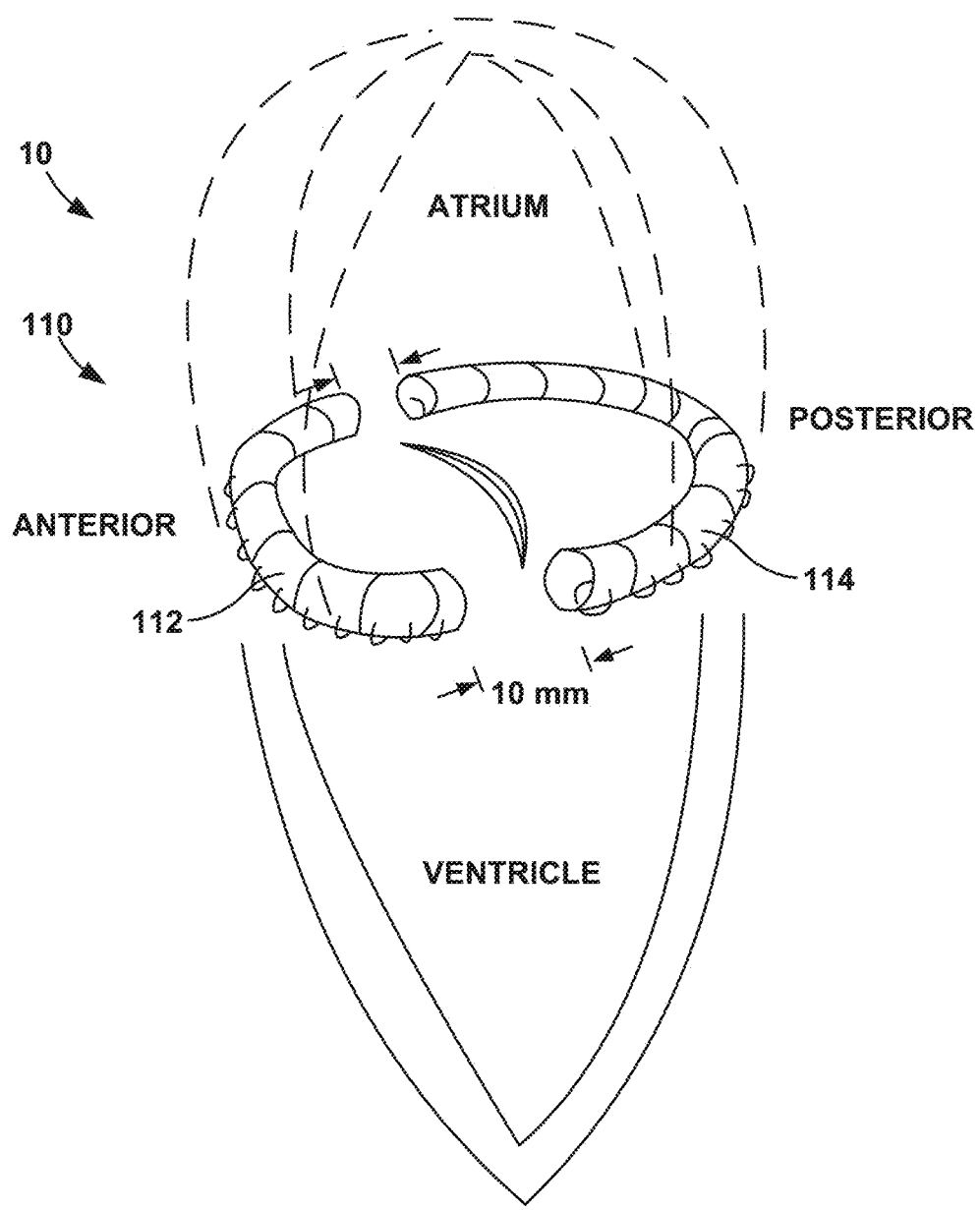
FIG. 10 is a schematic cross-sectional view of an example human heart and an annuloplasty device including a first tube-like structure and a second tube-like structure.

FIG. 10 is a schematic cross-sectional view of an example human heart 10 and an example annuloplasty device 110 including a first tube-like structure 112 and a second tube-like structure 114. Each of first tube-like structure 112 and second tube-like structure 114 may be similar to or substantially the same as tube-like structure 92 of FIG. 9 and may be engaged to a respective cinch wire and spiral anchor. In other examples, each of first tube-like structure 112 and second tube-like structure 114 may be similar to or substantially the same as any other tube-like structure described herein and may be anchored to tissue using any anchor(s) described herein. In some examples, a single cinch wire may extend through the respective bore of both first tube-like structure 112 and second tube-like structure 114 and be used to cinch both first tube-like structure 112 and second tube-like structure 114 toward each other. First tube-like structure 112 is configured to extend from adjacent a first trigone to adjacent a second trigone of the cardiac or vascular valve in a first direction, and second tube-like structure 114 is configured to extend from adjacent the first trigone to adjacent the second trigone of the cardiac or vascular valve in a second direction opposite the first direction. In this way, both sides of the cardiac or vascular valve may be pulled to respective sets of helical anchors, increasing coaptation of the valve leaflets.

Figure 11:
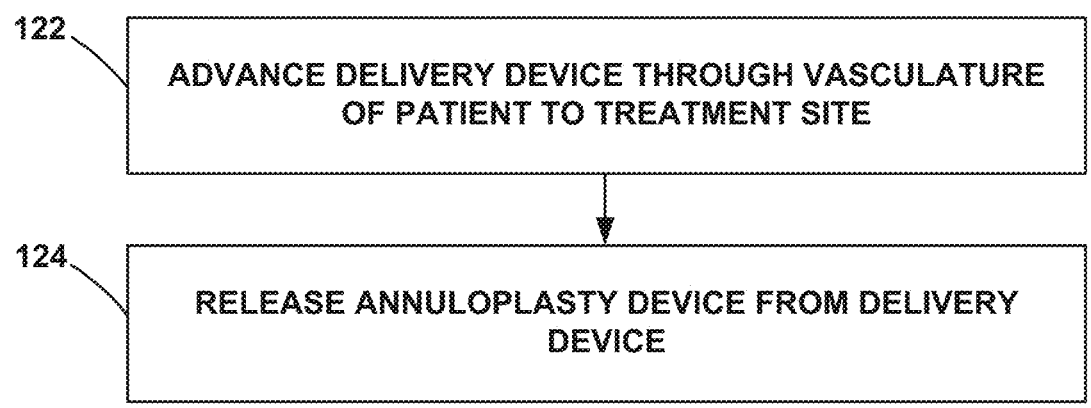
FIG. 11 is a flow diagram illustrating a technique for implanting an annuloplasty device.

FIG. 11 is a flow diagram illustrating an example technique for implanting an annuloplasty device. The technique of FIG. 11 will be described with concurrent reference to annuloplasty device 20 of FIG. 2, although it will be understood that the technique of FIG. 11 may be used to implant any of the annuloplasty devices described herein, and the annuloplasty devices described herein may be implanted using other techniques.

First, delivery device 26 may be advanced through vasculature of a patient to a treatment site (122). For example, a clinician may introduce delivery device 26 into vasculature of a patient transcutaneously. For instance, delivery device 26 may be introduced to a femoral or radial artery. Delivery device 26 may be advanced through vasculature of the patient to the treatment site by a clinician manipulating a handle of delivery device 26. In some examples, delivery device 26 may include a steerable shaft or tip to allow the clinician to direct delivery device 26 through bends, curves, and branching points of the vasculature.

In some examples, the treatment site may include the mitral valve, and delivery device 26 may be advanced to the left atrium. In other examples, the treatment site may include another heart valve. Delivery device 26 may access the left atrium trans-septally, trans-aortically, or trans-apically. In some examples, delivery device 26 may be tracked over a guide wire, through a guide catheter, or the like as delivery device 26 is advanced to the treatment site. Delivery device 26 may include one or more radiological markers at or near a distal end of delivery device 26 to assist visualizing delivery device 26 as delivery device is advanced to the treatment site.

Once delivery device 26 (e.g., a distal portion of delivery device 26) has been advance to the treatment site, delivery device 26 may release annuloplasty device 20, including tube-like structure 22 and the at least one anchor (124). The particular way in which tube-like structure 22 is released by delivery device 26 may depend on the configuration of tube-like structure, the at least one anchor, and whether a cinch wire, cinch device, or stylet is present. Examples of how delivery device 26 releases annuloplasty device 20 are described throughout this disclosure and may be used alone or in any combination depending on the configuration of the annuloplasty device.

Releasing annuloplasty device 20 may include, for example, allowing tube-like structure 22 to return toward its pre-set shape in examples in which tube-like structure has a pre-set shape. As described above, the pre-set shape may be configured to decrease a distance between valve leaflets LF that extend from the annulus AN. Releasing annuloplasty device 20 additionally or alternatively may include moving the at least one anchor between an undeployed configuration in which the at least one anchor extends generally inward into a bore of tube-like structure 22 and a deployed configuration in which the at least one anchor extends generally outward away from the bore of the tube-like structure 22. In some examples, releasing annuloplasty device 20 may include expanding an expandable balloon 52 (FIG. 5) to exert a force on the at least one anchor to cause the at least one anchor to move from an undeployed configuration to a deployed configuration.

In some examples, releasing annuloplasty device 20 may include removing a removable stylet 84 (FIG. 8) from the bore of tube-like structure 22 to allow tube-like structure 22 to recover toward a pre-set shape having a smaller radius of curvature than a radius of curvature of the removable stylet 84. In some examples, releasing annuloplasty device 20 from the lumen of delivery device 26 may allow a cinch device 74 (FIG. 7) disposed in the bore of tube-like structure 22 to urge tube-like structure 22 toward smaller radius of curvature.

The following clauses illustrate example subject matter disclosed herein.

Clause 1. An annuloplasty device comprising: a tube-like structure configured to extend around at least part of a circumference of an annulus of a cardiac or vascular valve; and at least one anchor configured to anchor the tube-like structure to the annulus, wherein the tube-like structure is configured to decrease a distance between valve leaflets that extend from the annulus.

Clause 2. The annuloplasty device of clause 1, wherein the tube-like structure comprises a biocompatible shape memory alloy.

Clause 3. The annuloplasty device of clause 1, wherein the tube-like structure comprises at least one of a nickel-titanium alloy, stainless steel, or a cobalt-chromium alloy.

Clause 4. The annuloplasty device of any one of clauses 1 to 3, wherein the tube-like structure comprises at least one of a stent or a cut tube.

Clause 5. The annuloplasty device of clause 4, wherein the tube-like structure comprises the stent, and wherein the stent comprises a spiral pattern of crowns and connection nodes.

Clause 6. The annuloplasty device of clause 4, wherein the tube-like structure comprises the cut tube, and wherein the cuts extend in at least one of circumferential or longitudinal directions of the cut tube.

Clause 7. The annuloplasty device of clause 6, wherein at least some of the cuts comprise spiral cuts extending around a circumference of the tube-like structure.

Clause 8. The annuloplasty device of any one of clauses 1 to 7, wherein the tube-like structure has a pre-set shape.

Clause 9. The annuloplasty device of clause 8, wherein the pre-set shape is configured to urge at least some anchors of the plurality of anchors toward each other in a radially inward direction to decrease a distance between valve leaflets that extend from the annulus.

Clause 10. The annuloplasty device of clause 8, wherein the pre-set shape is configured to urge at least some anchors of the plurality of anchors away from each other in a radially outward direction.

Clause 11. The annuloplasty device of any one of clauses 1 to 10, wherein the tube-like structure is a first tube-like structure, further comprising a second tube-like structure coaxially arranged within the first tube-like structure, wherein the second tube-like structure comprises the at least one anchor.

Clause 12. The annuloplasty device of clause 11, wherein the at least one anchor extends radially outward through the first tube-like structure, and wherein the first tube-like structure urges the at least one anchor to engage with tissue.

Clause 13. The annuloplasty device of any one of clauses 1 to 10, wherein the tube-like structure comprises the at least one anchor.

Clause 14. The annuloplasty device of clause 13, wherein the at least one anchor is configured to move between an undeployed configuration in which the at least one anchor extends generally inward into a bore of the tube-like structure and a deployed configuration in which the at least one anchor extends generally outward away from the bore of the tube-like structure.

Clause 15. The annuloplasty device of clause 13, wherein the at least one anchor is biased to extend in a first direction relative to a longitudinal axis of the tube-like structure and extend generally outward away from the bore of the tube-like structure.

Clause 16. The annuloplasty device of any one of clauses 1 to 10, wherein the at least one anchor comprises a spiral anchor configured to extend spirally through holes in the tube-like structure.

Clause 17. The annuloplasty device of any one of clauses 1 to 16, further comprising a cinch wire extending through a bore of the tube-like device.

Clause 18. The annuloplasty device of clause 17, wherein the cinch wire extends through the bore from a first end of the tube-like device to a second end of the tube-like device.

Clause 19. The annuloplasty device of clause 17 or 18, wherein the at least one anchor comprise a first anchor coupled to a first end of the cinch wire and a second anchor coupled to a second end of the cinch wire, opposite the first end of the cinch wire.

Clause 20. The annuloplasty device of any one of clauses 1 to 16, further comprising a cinch device disposed in a bore of the tube-like structure, wherein the cinch device has a pre-set shape with a smaller radius of curvature than the tube-like structure.

Clause 21. The annuloplasty device of clause 20, wherein the cinch device comprises at least one of a shaped wire, a shaped stent, or a shaped tube.

Clause 22. The annuloplasty device of any one of clauses 1 to 16, further comprising a removable stylet, wherein the removable stylet comprises a pre-set shape approximating a shape of the annulus, wherein the removable stylet is removably disposed in a bore of the tube-like structure, and wherein removal of the removable stylet from the bore allows the tube-like structure to recover toward a pre-set shape having a smaller radius of curvature than a radius of curvature of the removable stylet.

Clause 23. The annuloplasty device of any one of clauses 1 to 22, wherein the tube-like structure is configured to extend from adjacent a first trigone to a second trigone of the cardiac or vascular valve.

Clause 24. The annuloplasty device of any one of clauses 1 to 22, wherein the tube-like structure is configured to extend around substantially an entire circumference of the annulus.

Clause 25. The annuloplasty device of any one of clauses 1 to 22, wherein the tube-like structure is a first tube-like structure configured to extend from adjacent a first trigone to a second trigone of the cardiac or vascular valve in a first direction, further comprising a second tube-like structure configured to extend from adjacent the first trigone to adjacent the second trigone of the cardiac or vascular valve in a second direction opposite the first direction.

Clause 26. The annuloplasty device of any one of clauses 1 to 25, wherein the cardiac or vascular valve comprises a mitral valve comprising a mitral annulus, an anterior valve leaflet, and a posterior valve leaflet, and wherein the tube-like structure is configured to extend around a circumference of the mitral annulus from proximate the anterior valve leaflet to proximate the posterior valve leaflet.

Clause 27. A system comprising: a delivery device configured to access vasculature of a patient; and the annuloplasty device of any one of clauses 1 to 26, wherein the delivery device is configured to house the annuloplasty device in a lumen and deliver the annuloplasty device to the annulus of the cardiac or vascular valve and engage the anchors to the annulus.

Clause 28. The system of clause 27, wherein the delivery device comprises a steerable shaft.

Clause 29. The system of clause 27 or 28, wherein the delivery device is configured to exert a force on the anchor to engage the anchor with the annulus.

Clause 30. The system of any one of clauses 27 to 29, wherein the anchor comprises the spiral anchor configured to extend spirally through holes in the tube-like structure, and wherein the delivery device is configured to torque the spiral anchor to advance the spiral anchor in engagement with the tube-like structure.

Clause 31. The system of any one of clauses 27 to 30, wherein the delivery device is configured to manipulate the cinch device to reduce a radius of curvature of the tube-like structure.

Clause 32. A method comprising: advancing a delivery device through vasculature of a patient to a vascular or cardiac treatment site, wherein the delivery device comprises a lumen housing an annuloplasty device, wherein the annuloplasty device comprises: a tube-like structure configured to extend around at least part of a circumference of an annulus of a cardiac or vascular valve; and at least one anchor configured to anchor the tube-like structure to the annulus, wherein the tube-like structure is configured to decrease a distance between valve leaflets that extend from the annulus; and releasing the annuloplasty device from the lumen to extend around at least part of a circumference of an annulus of a cardiac or vascular valve.

Clause 33. The method of clause 32, wherein the tube-like structure comprises a biocompatible shape memory alloy.

Clause 34. The method of clause 32, wherein the tube-like structure comprises at least one of a nickel-titanium alloy, stainless steel, or a cobalt-chromium alloy.

Clause 35. The method of any one of clauses 32 to 34, wherein the tube-like structure comprises at least one of a stent or a cut tube.

Clause 36. The method of clause 35, wherein the tube-like structure comprises the stent, and wherein the stent comprises a spiral pattern of crowns and connection nodes.

Clause 37. The method of clause 35, wherein the tube-like structure comprises the cut tube, and wherein the cuts extend in at least one of circumferential or longitudinal directions of the laser cut tube.

Clause 38. The method of clause 37, wherein at least some of the cuts comprise spiral cuts extending around a circumference of the tube-like structure.

Clause 39. The method of any one of clauses 32 to 38, wherein the tube-like structure has a pre-set shape, wherein the delivery device urges the tube-like structure away from the pre-set shape, and wherein releasing the annuloplasty device from the lumen allows the tube-like structure to return toward the pre-set shape.

Clause 40. The method of clause 39, wherein the pre-set shape is configured to decrease a distance between valve leaflets that extend from the annulus.

Clause 41. The method of any one of clauses 32 to 40, wherein the tube-like structure is a first tube-like structure, further comprising a second tube-like structure coaxially arranged within the first tube-like structure, wherein the second tube-like structure comprises the at least one anchor, and wherein releasing the annuloplasty device from the lumen allows the first tube-like structure to urge the at least one anchor to engage with tissue.

Clause 42. The method of any one of clauses 32 to 40, wherein the tube-like structure comprises the at least one anchor, and wherein releasing the annuloplasty device from the lumen allows the tube-like structure to deform to urge the at least one anchor to engage with tissue.

Clause 43. The method of any one of clauses 32 to 40, wherein the tube-like structure comprises the at least one anchor, wherein releasing the annuloplasty device from the lumen comprises moving the at least one anchor between an undeployed configuration in which the at least one anchor extends generally inward into a bore of the tube-like structure and a deployed configuration in which the at least one anchor extends generally outward away from the bore of the tube-like structure.

Clause 44. The method of clause 43, wherein the delivery device further comprises a balloon catheter, and wherein moving the at least one anchor between the undeployed configuration and the deployed configuration comprises expanding the balloon to exert a force on the at least one anchor.

Clause 45. The method of any one of clauses 32 to 40, wherein the tube-like structure comprises the at least one anchor, wherein the at least one anchor is biased to extend in a first direction relative to a longitudinal axis of the tube-like structure and extend generally outward away from the bore of the tube-like structure, and wherein releasing the annuloplasty device from the lumen comprises exerting a force on the tube-like structure in a direction of the bias to cause the at least one anchor to engage with tissue.

Clause 46. The method of any one of clauses 32 to 40, wherein the at least one anchor comprises a spiral anchor configured to extend spirally through holes in the tube-like structure, and wherein releasing the annuloplasty device from the lumen comprises torqueing the spiral anchor with the delivery device to advance the spiral anchor in engagement with the tube-like structure and engage the spiral anchor with tissue.

Clause 47. The method of any one of clauses 32 to 46, wherein the annuloplasty device further comprises a cinch wire extending through a bore of the tube-like device.

Clause 48. The method of clause 47, wherein the cinch wire extends through the bore from a first end of the tube-like device to a second end of the tube-like device.

Clause 49. The method of clause 47 or 48, wherein the at least one anchor comprise a first anchor coupled to a first end of the cinch wire and a second anchor coupled to a second end of the cinch wire, opposite the first end of the cinch wire, and wherein releasing the annuloplasty device from the lumen comprises engaging the first anchor and the second anchor to tissue.

Clause 50. The method of any one of clauses 47 to 49, wherein releasing the annuloplasty device comprises exerting a force on the cinch wire to cause the tube-like structure to decrease the distance between the valve leaflets that extend from the annulus.

Clause 51. The method of any one of clauses 32 to 46, wherein the annuloplasty device further comprises a cinch device disposed in a bore of the tube-like structure, wherein the cinch device has a pre-set shape with a smaller radius of curvature than the tube-like structure, and wherein releasing the annuloplasty device from the lumen allows the cinch device to urge the tube-like structure toward the smaller radius of curvature.

Clause 52. The method of clause 51, wherein the cinch device comprises at least one of a shaped wire, a shaped stent, or a shaped tube.

Clause 53. The method of any one of clauses 32 to 46, wherein the annuloplasty device further comprises a removable stylet, wherein the removable stylet comprises a pre-set shape approximating a shape of the annulus, wherein the removable stylet is removably disposed in a bore of the tube-like structure, and wherein releasing the annuloplasty device from the lumen comprises removing the removable stylet from the bore to allow the tube-like structure to recover toward a pre-set shape having a smaller radius of curvature than a radius of curvature of the removable stylet.

Clause 54. The method of any one of clauses 32 to 53, wherein the tube-like structure is configured to extend from adjacent a first trigone to a second trigone of the cardiac or vascular valve, and wherein releasing the annuloplasty device from the lumen comprises tracking the delivery device from the first trigone to the second trigone.

Clause 55. The method of any one of clauses 32 to 53, wherein the tube-like structure is configured to extend around substantially an entire circumference of the annulus, and wherein releasing the annuloplasty device from the lumen comprises tracking the delivery device around substantially the entire circumference of the annulus.

Clause 56. The method of any one of clauses 32 to 54, wherein the tube-like structure is a first tube-like structure configured to extend from adjacent a first trigone to a second trigone of the cardiac or vascular valve in a first direction, wherein releasing the annuloplasty device from the lumen comprises tracking the delivery device from the first trigone to the second trigone while releasing the first tube-like structure, further comprising tracking the delivery device from adjacent the first trigone to the second trigone of the cardiac or vascular valve in a second direction opposite the first direction while releasing a second tube-like structure.

Clause 57. The method of any one of clauses 32 to 56, wherein the cardiac or vascular valve comprises a mitral valve comprising a mitral annulus, an anterior valve leaflet, and a posterior valve leaflet, and wherein the tube-like structure is configured to extend around a circumference of the mitral annulus from proximate the anterior valve leaflet to proximate the posterior valve leaflet.

Various examples have been described. These and other examples are within the scope of the following claims.

What is claimed is:

1. A system comprising:
   a delivery device configured to access vasculature of a patient; and
   an annuloplasty device comprising:
      a tube-like structure configured to extend around at least part of a circumference of an annulus of a cardiac or vascular valve; and
      a spiral anchor configured to anchor the tube-like structure to the annulus, the spiral anchor being configured to extend spirally through a plurality of holes in the tube-like structure such that the spiral anchor extends longitudinally along at least a length of the tube-like structure,
   wherein the delivery device is configured to house the annuloplasty device in a lumen and deliver the annuloplasty device to the annulus of the cardiac or vascular valve and engage the anchors to the annulus, wherein the tube-like structure is configured to decrease a distance between valve leaflets that extend from the annulus, and wherein the delivery device is configured to torque the spiral anchor to advance the spiral anchor in engagement with the tube-like structure.

2. The system of claim 1, wherein the delivery device comprises a steerable shaft.

3. The system of claim 1, wherein the delivery device is configured to exert a force on the anchor to engage the anchor with the annulus.

4. The system of claim 1, wherein the delivery device is configured to manipulate a cinch device to reduce a radius of curvature of the tube-like structure.

5. An annuloplasty device comprising:
   a tube-like structure configured to extend around at least part of a circumference of an annulus of a cardiac or vascular valve; and
   a spiral anchor configured to extend spirally through a plurality of holes of the tube-like structure to anchor the tube-like structure to the annulus, wherein the spiral anchor extends longitudinally along at least a length of the tube-like structure, wherein the tube-like structure is configured to decrease a distance between valve leaflets that extend from the annulus.

6. The annuloplasty device of claim 5, wherein the tube-like structure comprises at least one of a stent, a stent having a spiral pattern of crowns and connection nodes, or a cut tube having cuts extending in at least one of circumferential or longitudinal directions of the cut tube.

7. The annuloplasty device of claim 5, wherein the tube-like structure is a first tube-like structure, further comprising a second tube-like structure coaxially arranged within the first tube-like structure, wherein the second tube-like structure comprises the at least one anchor, wherein the at least one anchor extends radially outward through the first tube-like structure, and wherein the first tube-like structure urges the at least one anchor to engage with tissue.

8. The annuloplasty device of claim 5, further comprising a cinch wire extending through a bore of the tube-like structure, wherein the cinch wire extends through the bore from a first end of the tube-like device to a second end of the tube-like device.

9. The annuloplasty device of claim 8, further comprising a first cinch anchor coupled to a first end of the cinch wire and a second cinch anchor coupled to a second end of the cinch wire, opposite the first end of the cinch wire.

10. The annuloplasty device of claim 5, wherein the tube-like structure is configured to extend from adjacent a first trigone to a second trigone of the cardiac or vascular valve.

11. The annuloplasty device of claim 5, wherein the tube-like structure is configured to extend around substantially an entire circumference of the annulus.

12. The annuloplasty device of claim 5, wherein the tube-like structure is configured to extend around a circumference of a mitral annulus of a mitral valve from proximate an anterior valve leaflet to proximate a posterior valve leaflet.

\* \* \* \* \*